United States Patent [19]

Bender et al.

[11] Patent Number: 4,650,902

[45] Date of Patent: Mar. 17, 1987

[54] 2-KETOSULFONAMIDES AND PROCESS FOR THEIR PREPARATION

[75] Inventors: Albert Bender, Nuremberg; Dieter Günther, Kelkheim; Lothar Willms, Unkel; Rainer Wingen, Frankfurt am Main, all of Fed. Rep. of Germany

[73] Assignee: Hoechst Aktiengesellschaft, Frankfurt am Main, Fed. Rep. of Germany

[21] Appl. No.: 624,937

[22] Filed: Jun. 27, 1984

[30] Foreign Application Priority Data

Jun. 30, 1983 [DE]  Fed. Rep. of Germany ....... 3323511

[51] Int. Cl.$^4$ ................. C07C 143/74; C07C 143/77; C07C 143/78
[52] U.S. Cl. ........................................ 564/80; 564/88; 564/92; 564/95; 564/98; 564/99
[58] Field of Search ....................... 564/80, 88, 92, 95, 564/99, 98

[56] References Cited

U.S. PATENT DOCUMENTS 4,448,988  5/1984  Günther ................................ 564/95

FOREIGN PATENT DOCUMENTS 0001051  2/1981  European Pat. Off. .

OTHER PUBLICATIONS

Studies on Chemotherapeutic Agents . I . Synthesis of Quinoline and Naphthyridine Sulfonamide or Phosphonic Acid Derivatives, by Yanagisawa et al., in 21 Chemical & Pharmaceutical Bulletin 1080-89 (1973).

Primary Examiner—Robert T. Bond
Attorney, Agent, or Firm—Curtis, Morris & Safford

[57] ABSTRACT

The invention relates to new 2-ketosulfonamides of the formula $$R^1-\overset{O}{\underset{}{C}}-\overset{R^2}{\underset{R^3}{C}}-SO_2N\overset{R^4}{\underset{R^5}{\diagdown}}$$

and to a process for their preparation, wherein the reaction mixtures obtained by reacting enamines of the formula $$R^1-\overset{\overset{R^6}{\diagdown}\overset{}{N}\overset{R^7}{\diagup}}{\underset{R^3}{C}}=\overset{R^2}{\underset{}{C}}$$

with sulfamoyl halides of the formula $$X-SO_2N\overset{R^4}{\underset{R^5}{\diagdown}}$$

are hydrolyzed to the 2-ketosulfonamides.

2 Claims, No Drawings

2-KETOSULFONAMIDES AND PROCESS FOR THEIR PREPARATION

2-Ketosulfonamides are important intermediates. For example, they are mentioned as starting materials for pigments or chemotherapeutics.

Two processes have hitherto been disclosed for the preparation of these compounds.

In one of these processes, the starting material used is a 2-hydroxysulfonamide, which is oxidized to the keto compound. Aliphatic short-chain 2-ketosulfonamides, in particular, can be prepared by this process. However, the process has the disadvantage that the 2-hydroxysulfonamides required for oxidation are only obtainable via unstable 2-hydroxysulfonyl chlorides which are difficult to prepare (cf. German Offenlegungsschrift No. 3,116,129).

In the second process, which is particularly suitable for the preparation of aromatic 2-ketosulfonamides, an appropriately substituted acetophenone is used as the starting material. This is converted to the corresponding sulfonic acid with sulfur trioxide. After reaction with phosphorus chlorides (for example phosphorus trichloride or phosphorus pentachloride) to give the sulfonyl chloride, the latter is reacted with amines to give the sulfonamide (cf. J. Amer. Chem. Soc. 75, 2525 (1953)).

However, the use of such reactive compounds as sulfur trioxide or phosphorus chlorides leads to side reactions which necessitate costly purification of the intermediates.

As a resut of these short comings, both processes are only of limited use for the preparation of 2-ketosulfonamides.

A process has now been found which makes it possible to prepare new 2-ketosulfonamides in a simple manner by reacting certain enamines with sulfamoyl halides and hydrolyzing the reaction product.

The invention thus relates to the process defined in the claims and to the 2-ketosulfonamides prepared by this process.

The 2-ketosulfonamides prepared according to the invention are compounds of the formula I $$R^1-\overset{O}{\underset{R^3}{\overset{\|}{C}}}-\overset{R^2}{\underset{}{\overset{|}{C}}}-SO_2N\overset{R^4}{\underset{R^5}{\diagdown}} \quad (I)$$

in which
$R^1$ denotes an unbranched or branched $C_2$–$C_{10}$ alkyl radical, an aryl-($C_1$–$C_2$)-alkyl radical or a phenyl radical which can be substituted by one or more identical or different $C_1$–$C_4$ alkyl, $C_1$–$C_4$ alkoxy, $C_1$–$C_4$ alkylthio, fluoro, chloro, bromo or phenyl radicals, and
$R^2$ denotes hydrogen or a branched or unbranched $C_1$–$C_{10}$ alkyl radical.
$R^1$ and $R^2$ can also form, together with the two adjacent carbon atoms, a 3-membered to 20-membered ring which can be substituted in any position by a $C_1$–$C_6$ alkyl or $C_6$–$C_{12}$ aryl radical or can be fused with a benzo radical which can be substituted in any position by a halogen atom or a $C_1$–$C_6$ alkyl, $C_1$–$C_4$ alkoxy, or $C_1$–$C_4$ alkylthio radical.

$R_3$ denotes hydrogen or an unbranched or branched $C_1$–$C_4$ alkyl radical.
$R^4$ and $R^5$ independently of one another denote hydrogen or a $C_1$–$C_6$ alkyl or $C_3$–$C_7$ cycloalkyl radical.
$R^4$ and $R^5$ can also denote a 3-membered to 7-membered ring together with the adjacent nitrogen atom. If $R^4$ denotes hydrogen, $R^5$ can also denote a phenyl, biphenyl or naphthyl radical which can be substituted by one or more identical or different $C_1$–$C_4$ alkyl radicals, $C_1$–$C_4$ alkoxy radicals or $C_1$–$C_4$ alkylthio radicals or halogen (fluorine, chlorine or bromine).

The protection does not include the compounds of the formula I in which
$R^1$ is a $C_1$–$C_4$ alkyl or phenyl radical and $R^2$, $R^3$, $R^4$ and $R^5$ denote hydrogen.
$R^1$ is a phenyl radical, $R^2$, $R^3$ and $R^4$ denote hydrogen and $R^5$ denotes a phenyl, cyclohexyl or n-butyl radical.
$R^1$ is a phenyl radical, $R^2$ denotes hydrogen, $R^3$ and $R^4$ denote a methyl radical and $R^5$ denotes a phenyl, cyclohexyl or n-butyl radical.
$R^1$ is a pentyl radical, $R^2$ and $R^3$ denote hydrogen and $R^4$ and $R^5$ denote a methyl radical.

The starting materials for the process according to the invention are enamines of the formula II $$R^1-\overset{}{\underset{R^3}{\overset{|}{C}}}=\overset{\overset{R^6}{\diagdown}\overset{}{\underset{}{N}}\overset{R^7}{\diagup}}{\underset{}{\overset{|}{C}}}\overset{}{\underset{}{\overset{|}{,}}} \quad (II)$$

in which $R^1$, $R^2$ and $R^3$ have the abovementioned meanings and $R^6$ and $R^7$ independently of one another denote hydrogen or a $C_1$–$C_{20}$ alkyl, $C_3$–$C_7$ cycloalkyl or $C_6$–$C_{10}$ aryl radical. $R^6$ and $R^7$ can also form a common 5-, 6- or 7-membered ring together with the adjacent nitrogen atom, or a 5-, 6- or 7-membered ring together with the adjacent nitrogen atom and an oxygen atom, a sulfur atom or a second nitrogen atom optionally substituted by hydrogen or by an alkyl, aralkyl or aryl radical.

The enamines II can be prepared by processes known in the literature (Enamines—Synthesis, Structure and Reactions, Ed. A. G. Cook, M. Dekker Inc., N.Y. London 1969).

Preferred compounds of the formula II are those in which $R^6$ and $R^7$ denote, together with the nitrogen atom, a dimethylamino, diethylamino, pyrrolidino, piperidino or morpholino radical.

The enamines are reacted with sulfamoyl halides of the formula III $$X-SO_2N\overset{R^4}{\underset{R^5}{\diagdown}} \quad (III)$$

in which
$R^4$ and $R^5$ have the abovementioned meanings and X denotes a halogen atom.

It is preferred to use the sulfamoyl chlorides (X=Cl). They can be prepared by processes known in the literature, for example by reacting alkylammonium chlorides with sulfuryl chloride (cf. Liebigs Ann. 729, 40 (1969)), by reacting alcohols with chlorosulfonyl isocyanate (cf.

German Offenlegungsschrift No. 2,401,819) or by chlorinating N-substituted sulfamic acid derivatives (cf. J. Org. Chem. 41, 4028 (1969)).

The enamine and the sulfamoyl halide are reacted in stoichiometric quantities or with an excess of one or other of the starting materials, preferably in a solvent which is inert under the reaction conditions, and preferably in the presence of an acid acceptor.

The reaction is carried out at a temperature of $-50°$ to 65° C., preferably $-30°$ to 20° C.

The solvents used are aliphatic and cycloaliphatic hydrocarbons, for example pentane, hexane, heptane or cyclohexane, aliphatic halogenohydrocarbons, for example methylene chloride, chloroform or trichloroethane, aliphatic or cycloaliphatic ethers, for example diethyl ether, diisopropyl ether, dioxane or tetrahydrofuran, aliphatic nitriles, for example acetonitrile, and aromatic hydrocarbons, for example benzene and toluene. It is preferred to carry out the reaction in aliphatic or cycloaliphatic ethers and especially in tetrahydrofuran.

Suitable acid acceptors are inorganic compounds such as alkali metal and alkaline earth metal carbonates, bicarbonates, oxides and hydroxides, or organic bases such as aliphatic or cycloaliphatic amines or aromatic nitrogen compounds. It is preferred to use tertiary amines and especially triethylamine.

Preferably, it is also possible to use the enamine as the acid acceptor, in a proportion of 2 to 2.2 mol of enamine per mol of sulfamoyl halide.

The reaction mixture is hydrolyzed, if appropriate after removal of the acid acceptor and/or changing of the solvent, and the 2-ketosulfonamides I can be separated from the reaction mixture in high purity.

The 2-ketosulfonamides can be separated from the resulting reaction mixture by reacting the mixture with water in the presence of catalytic, stoichiometric or excess quantities of acid or base, by reaction with water-containing organic solvents in the presence of catalytic, stoichiometric or excess quantities of acid or base, or by reaction with water-containing inorganic supports giving an acidic or basic reaction, such as kieselguhr, silica gel, aluminum oxide, ion exchangers and resins carrying functional groups. Preferably, the reaction mixture is reacted with excess quantities of 0.5 to 5N acid, if appropriate in the presence of small quantities of the abovementioned solvents. 1–2N hydrochloric or sulfuric acid is particularly preferred.

A preferred embodiment of the process is to hydrolyze the reaction mixture chromatographically on an acidic or basic support and thereby to carry out hydrolysis and purification in one step, in particular in the case of more readily soluble 2-ketosulfonamides. Silica gel is particularly preferred as the support.

In view of the complex mixtures and instability of the products obtained by reacting enamines with methylsulfamoyl or ethylsulfamoyl chloride (cf. Bull. Chem. Soc. Jpn. 52, 1102 (1979)), it was surprising that the reaction mixtures obtained from enamines of the formula II and sulfamoyl chlorides of the formula III could be converted directly to the 2-ketosulfonamides I, obtained in high purity, without isolation and purification of the expected intermediates. Using readily obtainable starting materials and involving simple reaction steps without costly purification operations, the process according to the invention represents a generally applicable synthesis for 2-ketosulfonamides.

The ketosulfonamides of the general formula I according to the invention are precursors for new plant-protection agents and pharmaceuticals. However, they also represent analogs of acylacetamides, which are in turn very important as coupling components for azo dyes and pigments.

The examples which follow are intended to illustrate the invention.

EXAMPLE 1

2-Oxocyclohexanesulfonamide

A solution of 16.7 g (0.1 mol) of morpholinocyclohexene in 200 ml of tetrahydrofuran was treated simultaneously, over a period of 2 hours, at $-50°$ C., with solutions of 12.7 g (0.11 mol) of sulfamoyl chloride and 11.1 g (0.11 mol) of triethylamine each in 100 ml of tetrahydrofuran, the mixture was brought from $-50°$ to 20° C. over a period of 2 hours and filtered, the filtrate was evaporated to dryness in vacuo and the residue was chromatographed on 400 g of silica gel with methylene chloride. After recrystallization from isopropanol, the main fraction yielded 9.7 g (54.8% of theory, based on enamine) of 2-oxocyclohexanesulfonamide of melting point 118°–119° C.

EXAMPLE 2

2-Oxocyclohexylsulfonic acid cyclohexylamide 20.8 g (0.105 mol) of cyclohexylaminosulfonyl chloride in 60 ml of tetrahydrofuran were added dropwise, over a period of 2 hours, at $-50°$ C., to a solution of 16.7 g (0.1 mol) of morpholinocyclohex-1-ene and 10.6 g (0.105 mol) of triethylamine in 150 ml of tetrahydrofuran, the mixture was brought to 20° C. over a period of 4 hours and filtered, the filtrate was evaporated to dryness in vacuo and the residue was chromatographed on 80 g of silica gel with methylene chloride. After crystallization from diisopropyl ether, the main fraction yielded 14.9 g (57.4%) of colorless crystals of melting point 105°–109° C.

EXAMPLE 3

N-Methyl-5-oxononane-4-sulfonamide 211 g (1 mol) of 5-morpholinonon-4-ene were dissolved in 1 liter of tetrahydrofuran. First 129.5 g (1 mol) of amidosulfonyl chloride in 300 ml of tetrahydrofuran and then 101 g (1 mol) of triethylamine were added dropwise to the solution, cooled to $-40°$ C. The mixture was left to warm up to 20° C. and the precipitated triethylammonium hydrochloride was filtered off. The solvent was then distilled off and the residue was stirred for one hour with a mixture of 1 liter of methylene chloride and 250 ml of 2N hydrochloric acid. The organic phase was separated off, dried with sodium sulfate and distilled. This gave 152.3 g (65% of theory) of a colorless oil of boiling point 135°–138° C. at 0.3 mbar.

EXAMPLE 4

2-(2,4-Dichlorophenyl)-2-oxoethanesulfonamide 128 g (0.5 mol) of 1-morpholino-1-(2,4-dichlorophenyl)-ethene were dissolved in 1 liter of methylene chloride. At $-40°$ C., first 58 g (0.5 mol) of amidosulfonyl chloride in 330 ml of methylene chloride and then 50.5 g (0.5 mol) of triethylamine were added dropwise to the solution, cooled to $-40°$ C. The mixture was left to warm up to 20° C. and the solvent was distilled off. The residue was stirred in 500 ml of 2N hydrochloric acid. After filtration, 93 g of crude product were obtained which, after recrystallization from isopropanol, yielded 48.1 g (35% of theory) of colorless crystals of melting point 136°–139° C.

EXAMPLE 5

3-Oxo-1,2,3,4-tetrahydronaphthalene-2-sulfonamide

A solution of 19.9 g (0.1 mol) of 2-pyrrolidino-3,4-dihydronaphthalene in 200 ml of tetrahydrofuran was treated, over a period of 1 hour, at −30° C., with a solution of 17.3 g (0.15 mol) of sulfamoyl chloride in 50 ml of tetrahydrofuran and then, at the same temperature, with a solution of 15.2 g (0.15 mol) of triethylamine in 50 ml of tetrahydrofuran, the mixture was brought to 20° C. within 3 hours and filtered, the filtrate was freed of solvent in vacuo and the residue was stirred with 200 ml of 2N HCl and 40 ml of $CH_2Cl_2$ for 24 hours. The solid obtained was recrystallized from isopropanol to give 16.9 g (74.6%) of a product of melting point 145°–146° C.

The compounds listed in Table 1 were obtained analogously.

TABLE 1

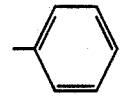

(I)

$$R^1-\underset{\underset{O}{\|}}{C}-\underset{\underset{R^3}{|}}{\overset{\overset{R^2}{|}}{C}}-SO_2N\underset{R^5}{\overset{R^4}{\diagup}}$$

| Example | $R^1$ | $R^2$ | $R^3$ | $R^4$ | $R^5$ | M.p. in °C. (B.p. in °C./mbar) |
|---|---|---|---|---|---|---|
| 6 | $CH_3-CH_2$ | $CH_3$ | H | H | H | 72–75 |
| 7 | $CH_3-CH_2$ | $CH_3$ | H | H | $CH_3$ | (128/0.2) |
| 8 | $CH_3-(CH_2)_2$ | $CH_3-CH_2$ | H | H | H | 68–71 |
| 9 | $CH_3-(CH_2)_2$ | $CH_3-CH_2$ | H | H | $CH_3$ | (130–135/0.2) |
| 10 | $CH_3-(CH_2)_3$ | $CH_3-(CH_2)_2$ | H | H | H | 69 |
| 11 | $CH_3-(CH_2)_4$ | $CH_3-(CH_2)_3$ | H | H | H | 54 |
| 12 | $(CH_3)_2CH$ | $CH_3$ | $CH_3$ | H | H | 104 |
| 13 | | $-(CH_2)_3-$ | H | H | H | 68 |
| 14 | | $-(CH_2)_3-$ | H | H | $CH_3$ | (140–150/0.1) |
| 15 | | $-(CH_2)_3-$ | H | H | $n-C_3H_7$ | (145–150/0.1) |
| 16 | | $-(CH_2)_4-$ | H | H | $CH_3$ | 72 |
| 17 | | $-(CH_2)_4-$ | H | H | $C_2H_5$ | (170–180/0.5) |
| 18 | | $-(CH_2)_4-$ | H | H | $n-C_3H_7$ | (190–200/0.5) |
| 19 | | $-(CH_2)_4-$ | H | H | $C(CH_3)_3$ | 88–90 |
| 20 | | $-(CH_2)_4-$ | H | H |  | 199 |
| 21 | $-CH(CH_3)-$ | $-(CH_2)_3-$ | H | H | $CH_3$ | 90 |
| 22 | $-(CH_2)_2-$ | $-CH(CH_3)CH_2-$ | H | H | $CH_3$ | 89 |
| 23 | $-(CH_2)_2-$ | $-CH(phenyl)CH_2-$ | H | H | H | 132 |
| 24 | $-(CH_2)_2-$ | $-CH(phenyl)CH_2-$ | H | H | $CH_3$ | 121 |
| 25 | | $-(CH_2)_5-$ | H | H | H | 76 |
| 26 | | $-(CH_2)_6-$ | H | H | H | 109 |
| 27 | | $-(CH_2)_{10}-$ | H | H | $CH_3$ | 135 |
| 28 | 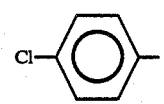 | H | H | H | $CH_3$ | 150 |
| 29 | 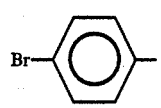 | H | H | H | H | 161 |
| 30 | 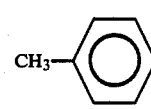 | H | H | H | H | 181 |
| 31 | 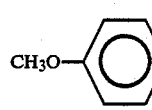 | H | H | H | H | 161 |
| 32 |  | H | H | H | H | 140 |

TABLE 1-continued $$R^1-\underset{\underset{O}{\|}}{C}-\underset{\underset{R^3}{|}}{\overset{\overset{R^2}{|}}{C}}-SO_2N\underset{R^5}{\overset{R^4}{\diagdown}} \quad (I)$$

| Example | R¹ | R² | R³ | R⁴ | R⁵ | M.p. in °C. (B.p. in °C./mbar) |
|---------|----|----|----|----|----|-------------------------------|
| 33 | phenyl | H | CH₃ | H | H | 149 |
| 34 | phenyl | —CH₂— | | H | H | 186 |
| 35 | —CH₂— | phenyl | | H | H | 167 |
| 36 | phenyl | —(CH₂)₂— | | H | H | 144 |
| 37 | phenyl | —(CH₂)₂— | | H | CH₃ | 141 |
| 38 | | phenyl-CH₂—CH₂— | | H | CH₃ | 105 |
| 39 | phenyl | —(CH₂)₃— | | H | H | 173 |

EXAMPLE 40

This example describes the preparation of an azo pigment from a 2-ketosulfonamide according to the invention and 2-nitro-4-chloroaniline.

3.44 g (20 mmol) of 4-chloro-2-nitroaniline in 10 ml of water and 4.2 ml of concentrated hydrochloric acid were diazotized with 2.8 ml of 40% sodium nitrite solution in 5 ml of water at 0°–5° C. After 30 minutes, excess nitrite was destroyed with amidosulfonic acid.

The diazonium solution prepared in this way was slowly added dropwise, at 0° C. and a pH of 9–10, to a solution of 4.67 g (20 mmol) of 4-chloro-β-sulfonamidoacetophenone in 30 ml of water and 15 ml of N-methylpyrrolidone. After 30 minutes, the mixture was treated with 30 ml of ice-water and the precipitated dye was filtered off under suction and dried. This gave 5 g of a yellow pigment of the formula

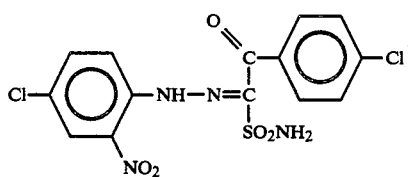

$C_{14}H_{10}Cl_2N_4O_5S$ (417.22)

λ: 422 nm, ε: 16,500 (DMF)

What is claimed is:

1. A process for the preparation of 2-ketosulfonamides of the formula I $$R^1-\underset{\underset{O}{\|}}{C}-\underset{\underset{R^3}{|}}{\overset{\overset{R^2}{|}}{C}}-SO_2N\underset{R^5}{\overset{R^4}{\diagdown}} \quad (I)$$

in which

R¹ is an unbranched or branched C₂–C₁₀ alkyl, aryl-(C₁–C₂)-alkyl, or phenyl unsubstituted or substituted by a $C_1$-$C_4$ alkyl, $C_1$-$C_4$ alkoxy, $C_1$-$C_4$ alkylthio or phenyl, or a halogen, $R^2$ is hydrogen or an unbranched or branched $C_1$-$C_{10}$ alkyl, or $R^1$ and $R^2$, together with the two adjacent carbon atoms, form a 3-membered to 20-membered ring which is unsubstituted or substituted in any position by $C_1$-$C_6$ alkyl or $C_6$-$C_{12}$ aryl or which can be fused with a benzo radical which is unsubstituted or substituted in any position by a halogen, $C_1$-$C_6$ alkyl, $C_1$-$C_4$ alkoxy, or $C_1$-$C_4$ alkylthio, $R^3$ is hydrogen or an unbranched or branched $C_1$-$C_4$ alkyl and $R^4$ and $R^5$, independently of one another, are hydrogen, $C_1$-$C_{10}$ alkyl or $C_3$-$C_7$ cycloalkyl, and if $R^4$ is hydrogen, $R^5$ is also phenyl, biphenyl or naphthyl, each unsubstituted or substituted by $C_1$-$C_4$ alkyl, $C_1$-$C_4$ alkoxy, $C_1$-$C_4$ alkylthio or halogen, wherein an enamine of the formula II

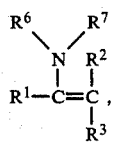
(II)

in which $R^1$, $R^2$ and $R^3$ have the above-mentioned meanings and $R^6$ and $R^7$, independently of one another, are hydrogen, $C_1$-$C_{20}$ alkyl, $C_3$-$C_7$ cycloalkyl or $C_6$-$C_{10}$ aryl, or $R^6$ and $R^7$, together with the adjacent nitrogen atom, is a dimethylamino, diethylamino, pyrrolidino, piperidino or morpholino which is reacted with a sulfamoyl halide of the formula III

(III)

in which $R^4$ and $R^5$ have the above-mentioned meanings and

X is a halogen, at a temperature of $-50°$ C. to $65°$ C. and the reaction product is hydrolyzed.

2. A 2-ketosulfonamide of the formula I

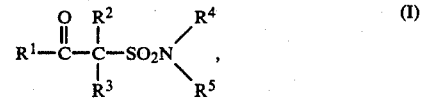
(I)

in which $R^1$ is an unbranched or branched $C_2$-$C_{10}$ alkyl, aryl-($C_1$-$C_2$)-alkyl or phenyl unsubstituted or substituted by a $C_1$-$C_4$ alkyl, $C_1$-$C_4$ alkoxy, $C_1$-$C_4$ alkylthio or phenyl, or a halogen, $R^2$ is hydrogen or an unbranched or branched $C_1$-$C_{10}$ alkyl, or $R^1$ and $R^2$, together with the two adjacent carbon atoms, form a 3-membered to 20-membered ring which can be fused with a benzo radical which is unsubstituted or substituted in any position by a $C_1$-$C_6$ alkyl, $C_6$-$C_{12}$ aryl, $C_1$-$C_4$ alkoxy, $C_1$-$C_4$ alkylthio, a halogen or hydrogen, $R^3$ is hydrogen or an unbranched or branched $C_1$-$C_4$ alkyl and $R^4$ and $R^5$, independently of one another, are hydrogen, $C_1$-$C_{10}$ alkyl or $C_3$-$C_7$ cycloalkyl, and if $R^4$ is hydrogen, $R^5$ is also phenyl, biphenyl or naphthyl, each unsubstituted or substituted by a $C_1$-$C_4$ alkyl, $C_1$-$C_4$ alkoxy or $C_1$-$C_4$ alkylthio, except for compounds of the formula I in which $R^1$ is a $C_1$-$C_4$ alkyl or phenyl and $R^2$, $R^3$, $R^4$ and $R^5$ are hydrogen, $R^1$ is phenyl, $R^2$, $R^3$ and $R^4$ are hydrogen and $R^5$ is phenyl, cyclohexyl or n-butyl, $R^1$ is phenyl, $R^2$ is hydrogen, $R^3$ and $R^4$ are methyl and $R^5$ is phenyl, cyclohexyl or n-butyl, and $R^1$ is pentyl, $R^2$ and $R^3$ are hydrogen and $R^4$ and $R^5$ are methyl.

* * * * *